United States Patent
Schödel et al.

[11] Patent Number: 6,116,902
[45] Date of Patent: Sep. 12, 2000

[54] MANUALLY OPERATED EJECTOR DEVICE FOR HOLDING A CARTRIDGE

[75] Inventors: Dieter Schödel, Wiesbaden; Steffen Oppawsky, Bad Homburg, both of Germany

[73] Assignee: Heraeus Kulzer GmbH & Co., KG, Hanau, Germany

[21] Appl. No.: 09/247,670

[22] Filed: Feb. 10, 1999

[30] Foreign Application Priority Data

Feb. 17, 1998 [DE] Germany .............................. 198 06 256

[51] Int. Cl.⁷ ...................................................... A61C 5/04
[52] U.S. Cl. ................................. 433/89; 433/90; 222/327
[58] Field of Search ...................... 433/89, 90; 604/232, 604/233, 234, 235, 275; 222/327, 386, 566, 43

[56] References Cited

U.S. PATENT DOCUMENTS

| | | | |
|---|---|---|---|
| 4,330,070 | 5/1982 | Doubleday | 222/43 |
| 4,472,141 | 9/1984 | Dragan | 433/90 |
| 4,619,613 | 10/1986 | Dragan | 433/90 |
| 5,061,179 | 10/1991 | Dragan | 433/90 |
| 5,743,431 | 4/1998 | Brattesari | 433/90 |

*Primary Examiner*—Pedro Philogene
*Attorney, Agent, or Firm*—Norris, McLaughlin & Marcus, P.A.

[57] ABSTRACT

A manually operated ejector receiving a cartridge containing viscous material, the chamber of which is provided with a lock for holding the cartridge, said lock being disposed for displacement in its lengthwise direction independently of the piston of the ejector.

20 Claims, 7 Drawing Sheets

MANUALLY OPERATED EJECTOR DEVICE FOR HOLDING A CARTRIDGE

The invention relates to a manually operated ejector device for holding a cartridge which is loaded with viscous material and which has a cylindrical portion at whose front end an outlet tip and at its back end an annular rim and an opening closed by a plunger that can be moved within the cartridge. The ejector device has a longitudinal barrel with an open front end and a back end, a piston disposed for longitudinal displacement within the barrel, a handle disposed at the back end of the barrel, and a lever which can be moved relative to the barrel and the handle, which is connected with a piston for the purpose of driving the piston in the barrel. The front end of the barrel has a lateral opening for the insertion of at least a portion of the cylindrical portion of the cartridge. The back end of the insertion opening forms a chamber with a diameter appropriate for containing the rim. The chamber has at its front end facing the open front end of the barrel a concentric abutment surface for the rim of the cartridge.

BACKGROUND OF THE INVENTION

Such ejector devices are disclosed in EP 063 891 B1 or in U.S. Pat. No. 5,489,207. These ejectors are used by the dentist, for example in order to fill a patient's dental cavities with viscous plastics as tooth filling material. For that purpose a cartridge containing the tooth filling material is placed in the insertion opening of the ejector device. When pressure is exerted on the lever, the piston is driven forward into the cartridge and drives the material out of the outlet tip of the cartridge. At times great pressure is needed in order to eject the material. If the cartridge is not correctly positioned, this force might destroy the cartridge or prevent it from remaining securely in its insertion opening. The cartridge might even be forced out of the insertion opening.

It is also known from U.S. Pat. No. 4,472,141, for example, to secure cartridges in the ejector devices or fasten the outlet tip with retaining nuts. This requires great material strength at the threads in order to prevent the threads from being torn out.

The present invention is addressed to the problem of improving an ejector device such that the cartridge will be securely held without requiring the dentist to perform additional manual operations after inserting the cartridge into the ejector device.

SUMMARY OF THE INVENTION

This problem is solved for an ejector device described in the beginning, in that on the back end of the chamber opposite the abutment surface a fixation means is disposed for displacement independently of the piston in its longitudinal direction, and is urged by the power of a spring in the direction of the chamber, and that the lock has on its end facing the chamber at least one contact surface which is intended to make contact with the back end of the cartridge.

An arrangement of this kind secures a solid seating of the cartridge within the ejector device, since it is virtually clamped in the ejector, even without a corresponding movement of the piston. The cartridge is placed in its position by this clamping and can not shift or rotate without an external application of force, so that when the dentist places the cartridge into the ejector device he can already define the position of the outlet tip thus assuring optimal handling in the patient's mouth. The dentist determines the position of the outlet tip that is best for him considering the position of the tooth cavity and considering its anatomic peculiarities. The lock secures the cartridge against unwanted rotation or dropping out.

It is especially advantageous that the lock is disposed between the chamber and an abutment piece disposed in the barrel, and that the back end of the spring is in contact with the abutment piece. Easy mounting and a secure abutment of the spring are achieved. In particular it is desirable that the lock be configured as a hollow cylinder around the piston, that the spring be disposed inside of the fixation means and that the hollow cylinder be open at its end remote from the chamber. Furthermore it is desirable that the lock and the abutment piece be arranged symmetrically with the axis of the piston, and that the abutment piece be of annular shape, since this assures a uniform, axially symmetrical application of force.

It is furthermore desirable that the piston have a safety abutment on the side of the abutment piece facing away from the lock, which is intended for contact with the abutment piece in order to limit the forward travel of the piston. This arrangement assures that the forward travel of the piston can be related to its depth of penetration in the cartridge. This limitation of the forward travel assures that the piston will not damage the front end of the cartridge or possibly break away from the rim of the cartridge. For in such a case it would be possible that a piece of the cartridge might be driven with great pressure into the patient's mouth and result in considerable injury.

The fixation means is best guided in the barrel. Furthermore, it is advantageous that the barrel have a front portion with an insertion opening, chamber and lock, and that the front portion be releasably fastened to the remaining part of the barrel. With such an arrangement, several different adapters can be provided, each having different insertion openings or chambers and/or different lock, and being interchangeable if necessary. In this manner the front portions of the barrel can be adapted to different cartridge shapes. In particular, the front portion can be joined by a screw thread to the remaining part of the barrel. It is advantageous that the front portion is held for rotation through a connecting sleeve on a coupling piece, the coupling piece being best connected releasably to the remaining part of the barrel. The ability to rotate permits a defined setting of the position of the outlet tip of the cartridge, since rotation of the cartridge within the chamber in the event of excessively high pressure from the lock is relatively difficult. A large coupling piece, however, can be more easily rotated.

According to an advantageous embodiment of the invention the front end of the lock facing the loading opening is configured as a truncated cone with a taper inclining at the front end toward the axis, and the taper extending into the chamber appropriate for the accommodation of the cartridge. The size of the front end of the taper (diameter, angle of inclination) can be made such that the front end of the taper is suitable and is designed for engaging in the opening of the cartridge or into an internal taper disposed at the opening. Thus the cartridge is given an additional hold in the chamber against displacement. The collar of the cartridge can also fit into an undercut at the front end of the chamber, which surrounds the abutment surface.

In another embodiment of the invention the fixation means is configured as a cylinder whose circumferential surface, at least at a portion of the cylinder's circumference, reaches out beyond the contact surface for the cartridge and into the chamber, and the barrel has in the area of the cylinder's circumference slide openings which permit grasping the circumference of the fixation means in order to shift the latter in the axial direction. In that case the diameter of the contact surface is best at least slightly larger than the diameter of the collar of the cartridge. Advantageously, a plurality of slide openings are uniformly distributed about the circumference of the barrel. Such an arrangement makes it possible for the cartridge, when inserted into the ejector device, to be surrounded at its back end by the lock, so that the possibility of any lateral displacement of the cartridge is ruled out. By means of the slide openings the dentist can grasp the outer surface of the lock and pull it back, so that the opening of the chamber for the insertion of the cartridge is released. For this purpose it may be desirable for the outer surface of the lock to be rough, at least in the area of the slide openings, in order to prevent the dentist's fingers from slipping during use.

Instead of the dentist's direct engagement of the slide openings, a sliding ring can be disposed around the barrel, which is connected through the slide openings to the lock, so that the dentist engages the externally situated sliding ring. This substantially improves comfort in operation because, among other things, the sliding ring presents a larger surface to grasp.

To connect the sliding ring to the lock it is advantageous that the lock has on its cylindrical surface, underneath the slide opening and corresponding thereto, ball socket openings in which balls are arranged on a portion of its circumference, the balls extending through the slide openings into recesses in the sliding ring, which in turn likewise receive a portion of the spherical surface. Both the ball sockets and the recesses in the sliding ring are matched in shape and size, but at least in their extension along the longitudinal axis of the ejector device, to the size of the portion of the ball that is to be received, in order to assure the closest possible fit of the corresponding spherical sections in the sliding ring and lock respectively. Ideally, the ball sockets and the recesses in the sliding ring are also configured as spherical sections with a radius corresponding to the radius of the balls.

The ball sockets can also be configured as blind holes. In that case the bottom of the blind holes can expediently be formed by the mantle surface of a supporting sleeve disposed within the lock.

BRIEF SUMMARY OF THE DRAWINGS

Embodiments of the invention will be explained with the aid of a drawing, wherein.

Figure 1:
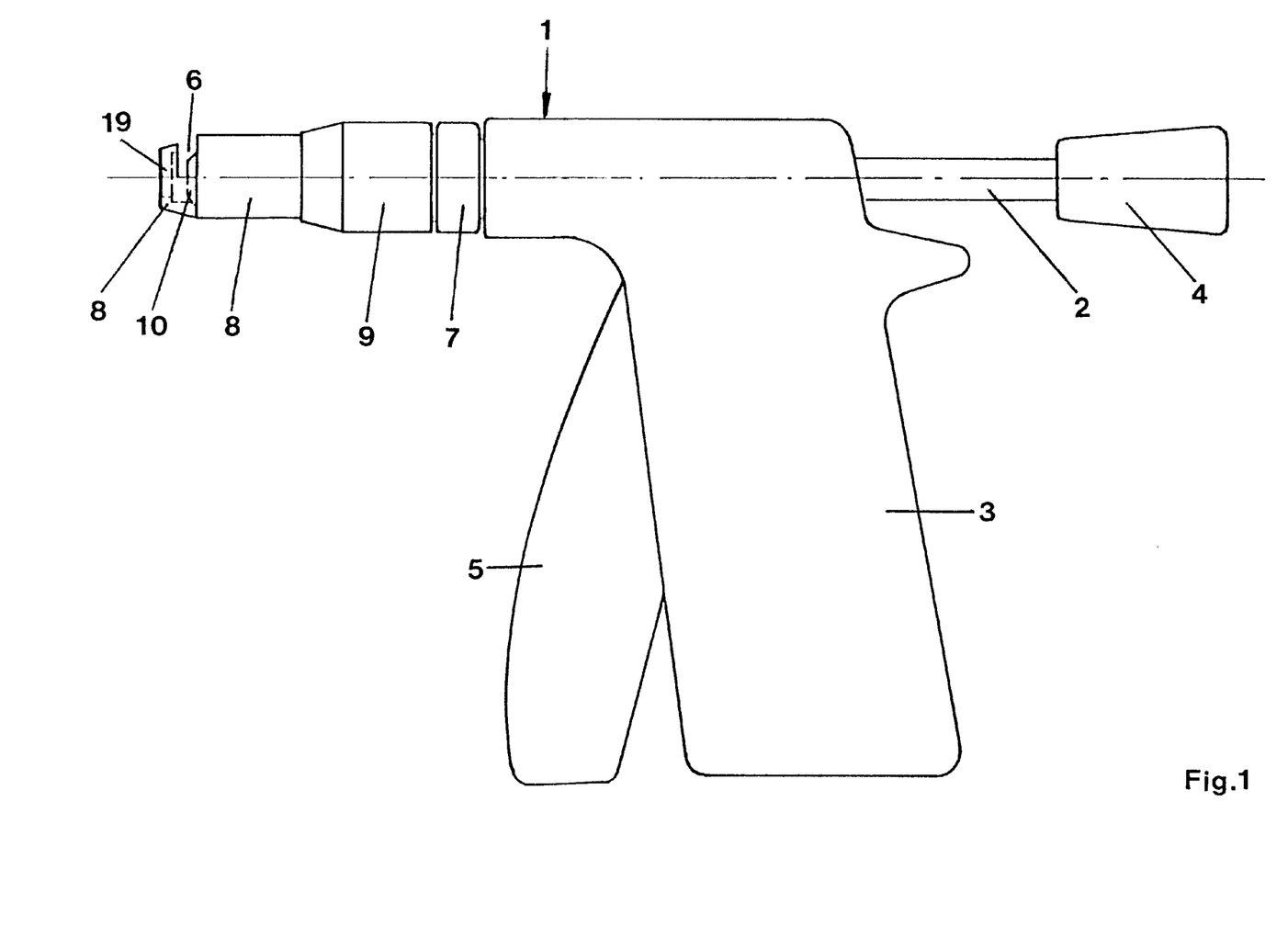
FIG. 1 shows an embodiment of the ejector device.
Figure 2:
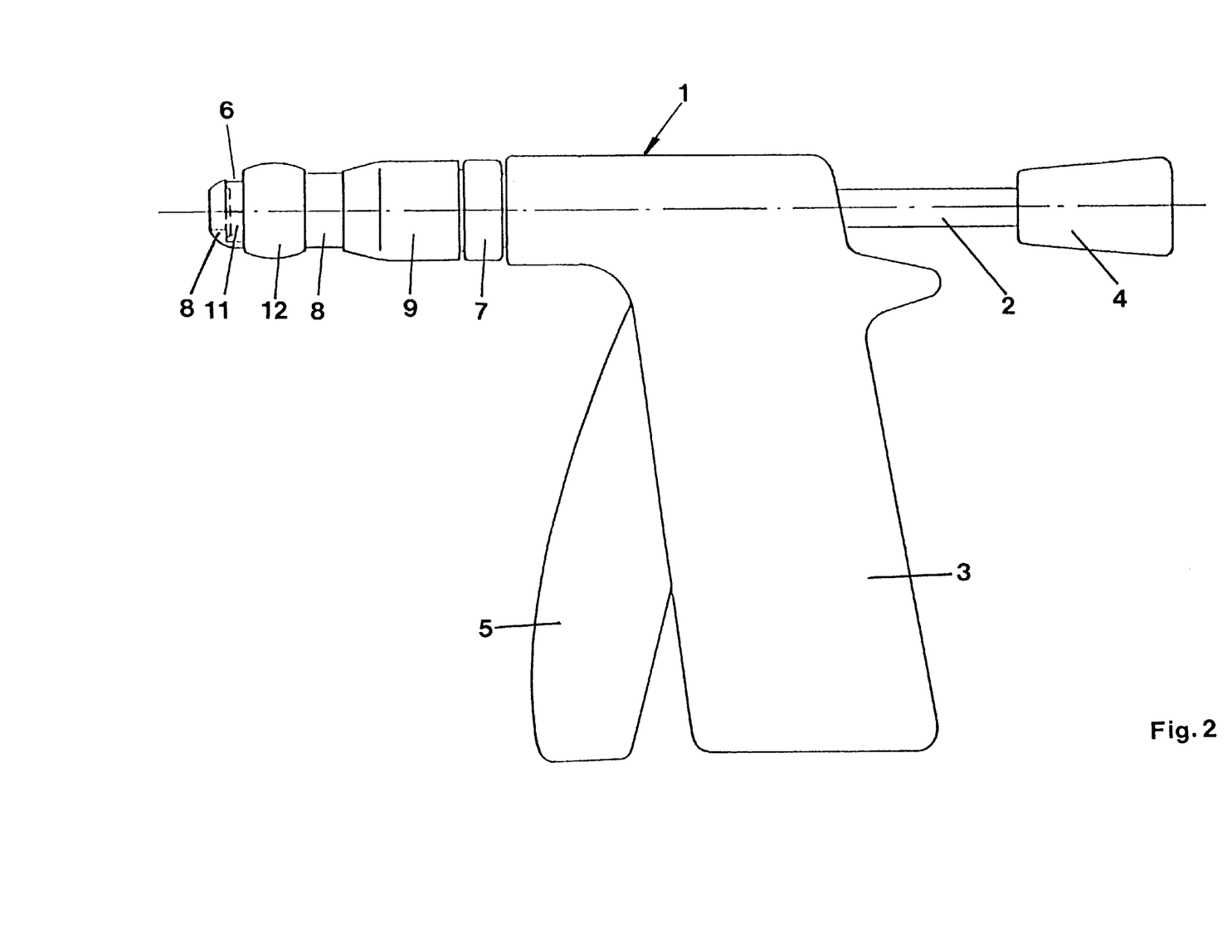
FIG. 2 another embodiment of the ejector device.

The ejector device represented in FIGS. 1 and 2 has a barrel 1 within which a longitudinally displaceable piston 2 is disposed. The piston 2 extends out of the barrel 1 at the back end of the ejector device on which a handle 3 is disposed. The piston 2 has at its back end a grip 4 by which it can be drawn back. This rearward movement is necessary in order to retract the piston 2 out of the cartridge 15 after the ejector device has been used, and to release the cartridge for removal from the ejector device. A lever 5 which is movable against the handle 3 and against the barrel 1. The lever 5 is engaged with the piston 2 in any desired manner, as for example the one disclosed in U.S. Pat. No. 4,472,141, in order to drive the piston 2 in the barrel 1. By this movement the piston 2 is driven forward toward the chamber 6, and consequently into the cartridge 15 disposed in chamber 6 and not represented in FIGS. 1 and 2, in order to force the material in cartridge 15 out of the nozzle of the latter by means of the plunger located in the chamber 6.

The front portion 8 of the barrel 1 is screwed by means of a coupling 7 to the rest of the barrel 1. It has a connecting sleeve 9 by which the front portion is fastened with the chamber 6 and cartridge 15 to the coupling 7. First it can be rotated to adjust the position of the nozzle. In FIG. 1 the bevel 10 within the chamber 6 is indicated; in another embodiment of the invention, in FIG. 2, the cylinder 11 of the fixation means 13 is shown within the chamber 6, which can be shifted axially with the ring 12.

Figure 3:
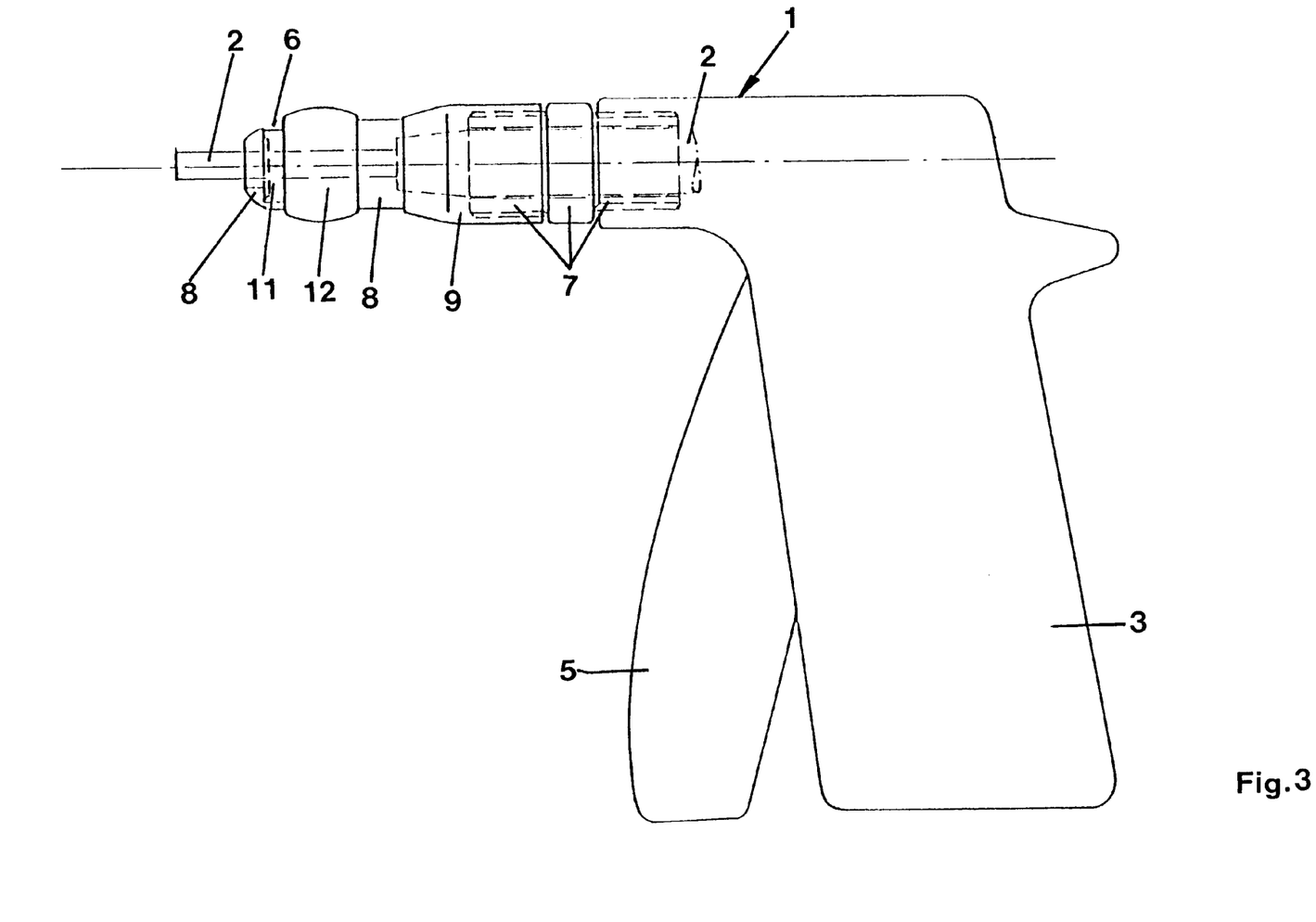
FIG. 3 an ejector device with an internal view in phantom.
Figure 4:
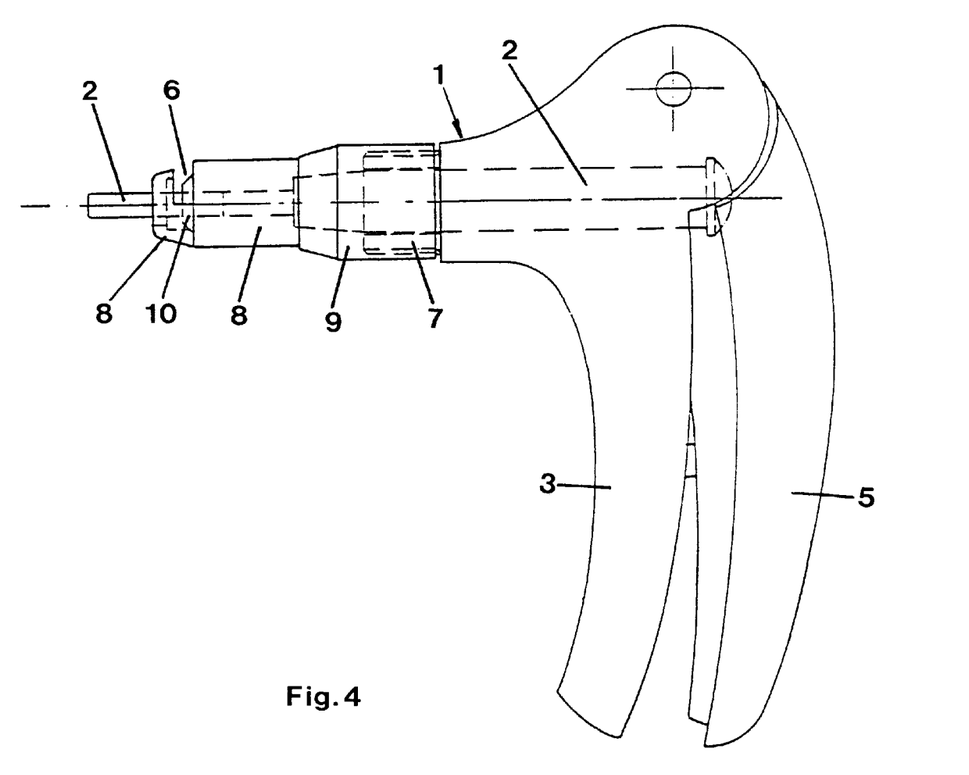
FIG. 4 an ejector device in another embodiment.
Figure 5:
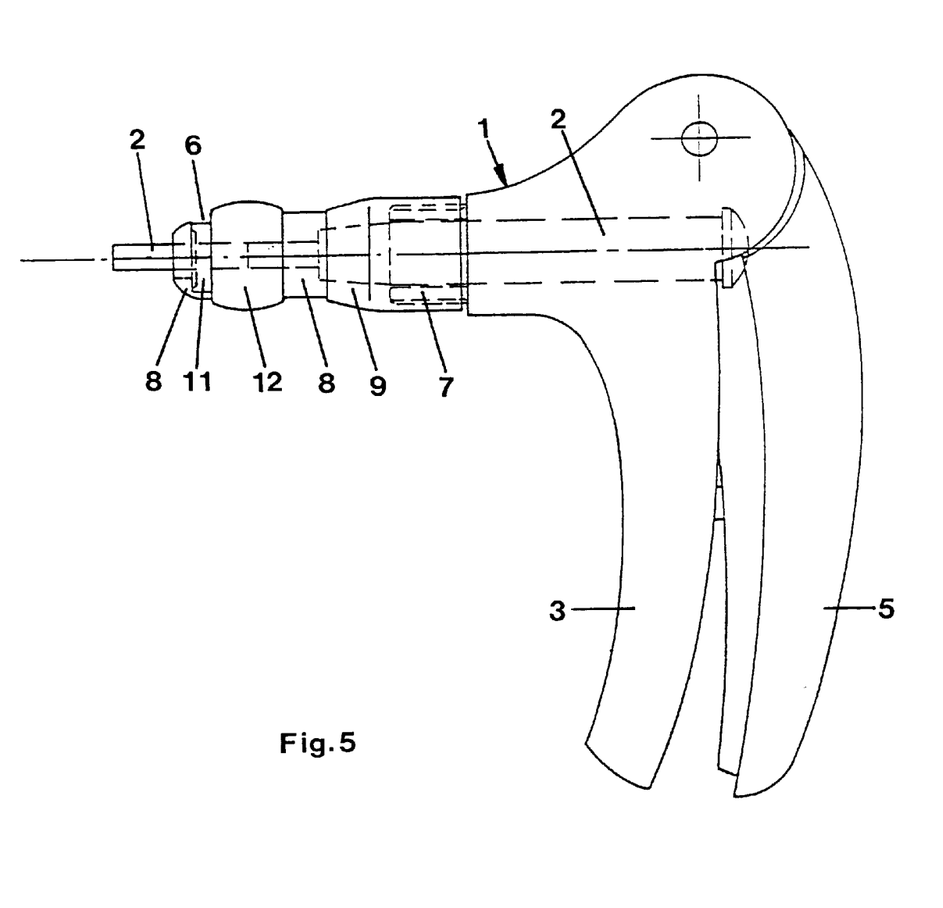
FIG. 5 another ejector device.

FIG. 3 shows the ejector device of FIG. 2, but with the complete coupling 7. The piston 2 is shown in the retracted state, as shown also in FIG. 6. FIG. 4 shows an ejector device with the cartridge chamber shown in FIGS. 1 and 5, but with a different handle 3 as well as a different barrel 1. The coupling 7 is affixed to the rear part of the barrel 1; the connecting sleeve 9 joins this coupling 7 to the front part 8 of the barrel 1. A similar ejector device is represented in FIG. 5, the front part 8 of the barrel 1 corresponding to the one shown in FIGS. 2, 3 and 7.

Figure 6:
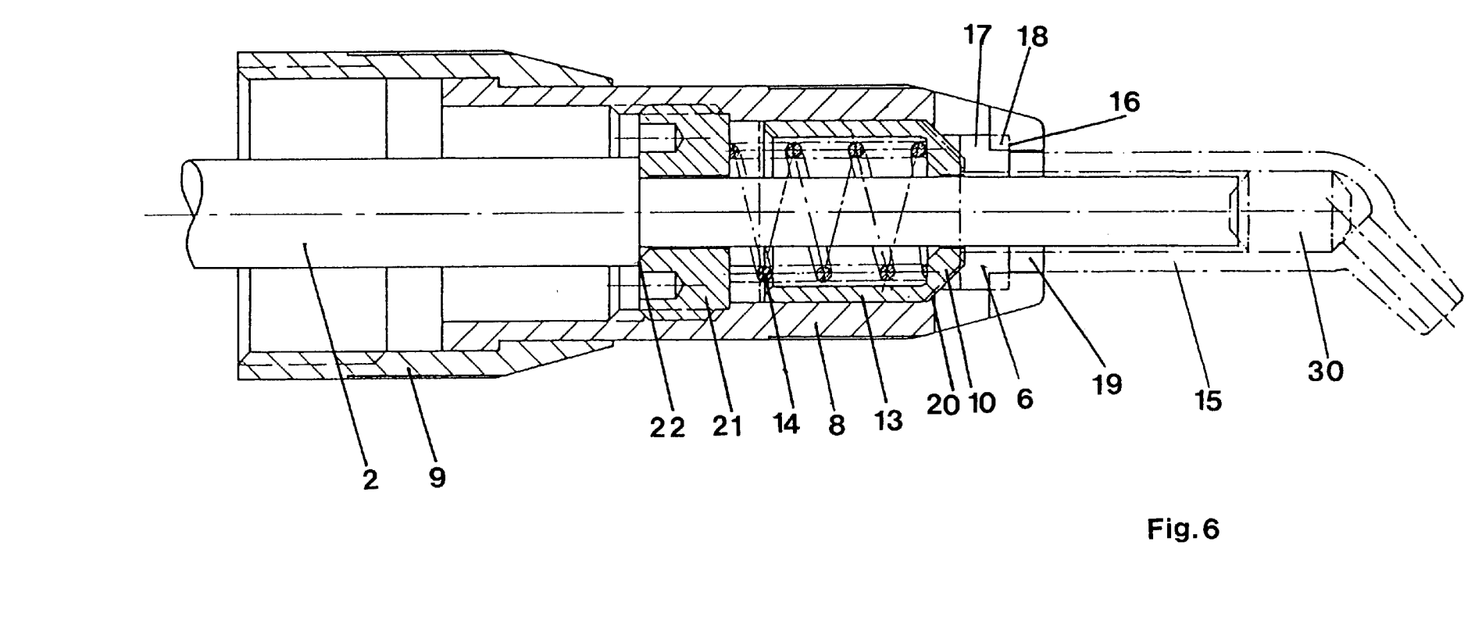
FIG. 6 the front end of the barrel with the lock in a first embodiment.
Figure 7:
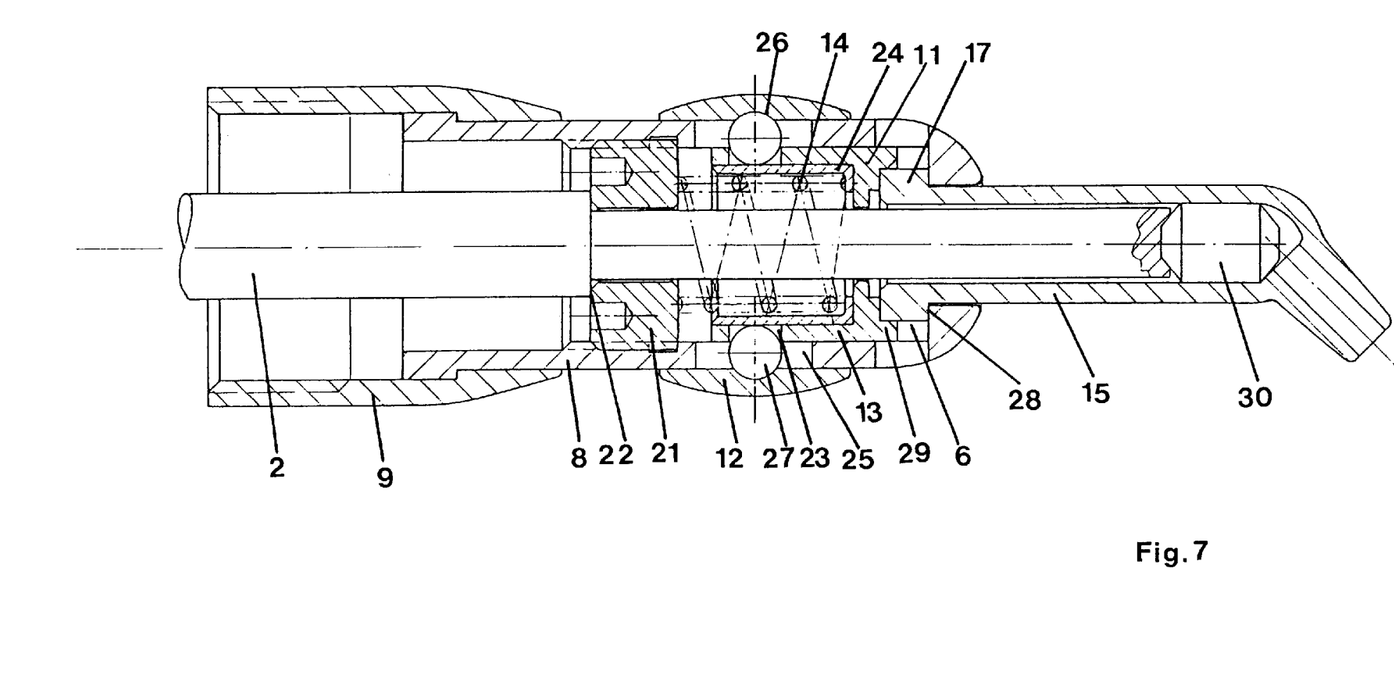
FIG. 7 the front end of the barrel in another embodiment.

Details of the front part 8 of the barrel 1 are represented in FIGS. 6 and 7 for two different embodiments of the invention. FIG. 6 shows an embodiment with a fixation means 13 having a bevel 10 at its front end. The lock 13 is of substantially cylindrical shape and is displaceable within the front part 8 of the barrel 1. Within the cylinder of the fixation means 13 there is a spring 14 which urges the lock 13 with a force directed toward the front end of the ejector device. By this force the bevel 10 is forced into the chamber 6 and, if a cartridge 15 is loaded, it contacts the back end of the cartridge 15. For this purpose the contact surface 16 can be planar and disposed at right angles to the longitudinal axis of the cartridge 15. However, it is also possible to provide the cartridge 15 with an internal bevel at its rear opening, against which the bevel 10 of the lock 13 is pressed. The cartridge 15 has at its back end a collar 17 which engages an undercut 18 which is formed at the front end of the chamber 6. By the cooperation of the undercut 18 with the bevel 10, the collar 17 of the cartridge 15 is held securely in the ejector device. The cylindrical part of the cartridge 15 lies at the front end of the front part 8 of the barrel in a lateral insertion opening 19. The front part of cartridge 15 is of nearly any desired shape. Many different forms are sufficiently well known to the man of the art (for example in EP 063 891 B1). In FIGS. 6 and 7 is shown a conventional cartridge 15 in which the piston 2 is forced into the cylinder of the cartridge 15 in order to force the material out of the cartridge by means of the plunger 30. The length of the movement of the lock 13 within the barrel 1 is limited by an inwardly facing flank 20 which is in contact with the bevel 10 of the lock 13 when the cartridge is not inserted, and thus assures that actually only the bevel 10 extends into the chamber 6. Thus, when the cartridge 15 is inserted into the barrel 1 the assurance is given that the cartridge 15 will press against the bevel 10 and not against the cylindrical part of the lock 13. When pressure is exerted on the bevel 10, the latter is driven out of the chamber 6 against the spring force, so that the cartridge 15 can be laid into the lateral insertion opening 19 and chamber 6. As soon as the cartridge 15 is correctly inserted, it is forced forward by the lock 13, so that the collar 17 slips into the undercut 18 and thus the cartridge 15 is affixed. At its back end the spring 14 thrusts against the abutment piece 21 which annularly surrounds the axis of the piston 2 and receives the latter in a central bore. The piston 2 itself has a safety abutment 22 which limits the travel of piston 2 toward the front part 8 of the barrel 1, since in this forward position it is in contact with the back end of the abutment 21. The piston 2 can therefore be withdrawn rearwardly out of the ejector device, but it cannot be pressed forward to an unlimited degree, so as to prevent any unlimited advance of piston 2 from extending too far into the cartridge 15. In this manner the cartridge 15 is prevented from bursting due to the pressure of the piston 2.

Details of another embodiment of the invention are shown in FIG. 7. The basic construction is similar to the one shown in FIG. 6, only the lock 13 and its displacement mechanism are differently made. Moreover, the chamber 6 has no undercut to receive the collar 17 of the cartridge 15. The lock 13 is in the form of a cylinder 11 all the way to its front end. The peripheral surface of the cylinder 11 reaches at its front end past the contact surface 16 for the cartridge 15 and into the chamber 6. Thus the front end of the peripheral surface clutches the collar 17 of an inserted cartridge 15 and secures it in the lateral insertion opening 19 and chamber 6 of the front part 8 of the barrel 1. The front end of the peripheral surface of the lock 13 does not necessarily need to extend over the entire periphery of the cylinder beyond the contact surface 16: extension distributed over the circumference of the cylinder 11 of the lock, with a meander-shaped front face, for example, will also suffice, as a rule. The lock 13 has blind holes 23 distributed over its circumference, which are formed by boring through the lock 13 at the appropriate points and then introducing a supporting sleeve 24 into the lock. As seen from the axis of the barrel 1, above the blind holes 23 the barrel 1 has slide openings 25. In the area of the slide openings 25 the sliding ring 12 is disposed around the barrel 1 on its front portion 8. The sliding ring 12 has on its interior recesses 26 corresponding to the blind holes 23. In each case a ball 7 is disposed in these recesses 26 and in the associated blind hole 23. The recesses 26 are cupped, with a radius corresponding approximately to the radius of the balls 27. The balls 27 reach from the recesses 26 into the blind holes 23, their circumference being supported on the outer edges of the blind holes 23. The slide openings 25 are larger in their reach along the barrel 1 than the diameter of the balls 27 so as to permit the balls 27 to move within the slide openings 25 and thus permit a movement of the lock 13 guided by the sliding ring 12. The length of the slide openings 25 in the direction of the length of the barrel 1 will depend on the required length of the displacement of the lock 13 and is at least precisely as great, and better slightly greater, than this length.

For the insertion of the cartridge 15 into the ejector device the lock 13 is pulled back by means of the sliding ring 12 out of the chamber 6. The cartridge 15 can then be introduced into the lateral insertion opening 19 and the chamber 6. When the sliding ring 12 is released, the lock 13 is urged by the force of spring 14 toward the cartridge 15. The contact surface 16 comes to rest against the back of the cartridge 15 and presses it against the abutment surface 28. The end 29 of the cylinder 11 of the lock 13 clutching the rim 17 holds the cartridge 15 securely in the ejector device.

We claim:

1. Manually operated ejector device for receiving a cartridge which is loaded with viscous material and has a cylindrical portion at whose front end an outlet tip is disposed and at whose back end an annular rim and an opening blocked by a plunger movable within the cartridge are provided, the ejector device having an elongated barrel with an open front end and a back end, a piston disposed for longitudinal displacement in the barrel, a handle disposed at the back end of the barrel, and a lever which can be moved relative to the barrel and the handle and is connected with the piston in order to move the piston within the barrel, the front end of the barrel having a lateral insertion opening to receive at least a portion of the cylindrical part of the cartridge, the back end of the insertion opening forming a chamber with a diameter appropriate for receiving the rim and the chamber having at its front end facing the open end of the barrel a concentric abutment surface for the rim of the cartridge, wherein at the back end of the chamber (6) opposite the abutment surface (28) a lock (13) is disposed for displacement in the lengthwise direction of the chamber independently of the piston (2) and is biased by a spring (14) toward the chamber (6), and that the lock (13) has at the end of the lock facing the chamber at least one contact surface (16) which is intended for contact with the back end of the cartridge (15).

2. Ejector device according to claim 1, wherein the lock (13) is disposed between the chamber (6) and an abutment piece (21) disposed within the barrel (1) and that the spring (14) is in contact at the back end of the spring with the abutment piece (21).

3. Ejector device according to claim 1 the lock (13) is configured as a hollow cylinder around the piston (2), that the spring (14) is disposed in the interior of the lock (13), and that the hollow cylinder is open at its end facing away from the chamber (6).

4. Ejector device according to claim 2 the lock (13) and the abutment piece (21) are disposed symmetrically to the axis of the piston (2) and that the abutment piece (21) is ring-shaped.

5. Ejector device according to claim 1 the piston (2) has on the end of the abutment piece (21) facing away from the lock (13) a safety abutment (22) which is intended for contact with the abutment piece (21) in order to limit the forward travel of the piston (2).

6. Ejector device according to claim 1 the lock (13) is guided in the barrel (1).

7. Ejector device according to claim 1 the barrel (1) has a front portion (8) with an insertion opening (19), chamber (6) and lock (13), and that the front portion (8) is connected releasably with the remaining portion of the barrel (1).

8. Ejector device according to claim 7, the front portion (8) is mounted for rotation by a connecting sleeve (9) on a coupling piece (7).

9. Ejector device according to claim 8, the coupling piece (7) is releasably joined to the remaining portion of the barrel (1).

10. Ejector device according to claim 7 the front portion (8) is connected by a screw thread to the remaining portion of the barrel (1).

11. Ejector device according to claim 1 the front end of the lock (13) facing the insertion opening is configured as a truncated cone with a bevel (10) at the front end sloping toward the axis and that the bevel (10) reaches into the chamber (6) suitable for accommodating the cartridge (15).

12. Ejector device according to claim 11, wherein the front end of the bevel (10) is provided for engagement in the opening of the cartridge (15) or engagement in an internal bevel disposed at the opening.

13. Ejector device according to claim 1 the lock (13) is configured as a cylinder whose circumferential surface reaches, at least at a portion of the cylinder circumference, beyond the contact surface (16) toward the insertion opening (19), and into the chamber (6), and that the barrel (1) has in the area of the cylinder circumference, slide openings (25) which permit access to the circumferential surface of the lock (13) in order to shift the latter in the axial direction.

14. Ejector device according to claim 13, the diameter of the contact surface (16) is at least slightly greater than the diameter of the rim (17) of the cartridge.

15. Ejector device according to claim 13 a plurality of slide openings (25) are uniformly distributed about the circumference of the barrel (1).

16. Ejector device according to claim 13 in the area of the slide openings (25) around the barrel (1) a sliding ring (12) is disposed which is connected through the slide openings (25) with the lock (13).

17. Ejector device according to claim 16, the lock (13) has on said cylindrical circumferential surface, underneath the slide opening (25) and corresponding thereto, ball socket openings in which balls (27) are disposed on a portion of its circumference, the balls (27) reaching through the slide openings (25) into recesses (26) in the sliding ring (12).

18. Ejector device according to claim 17, the ball socket openings are configured as blind holes (23).

19. Ejector device according to claim 18, the bottom of the blind holes (23) is formed by the circumferential surface of a supporting sleeve (24) disposed within the lock (13).

20. Ejector device according to claim 17 the recesses (26) are configured in the sliding ring (12) as a spherical cup section whose radius is at least equal to the radius of the balls (27).

* * * * *